(12) United States Patent
Schmidt

(10) Patent No.: US 8,445,220 B2
(45) Date of Patent: May 21, 2013

(54) METHODS OF DIAGNOSING LATENT AND ACTIVE MALIGNANCIES

(71) Applicant: Geoffrey Schmidt, Norwell, MA (US)

(72) Inventor: Geoffrey Schmidt, Norwell, MA (US)

(73) Assignee: ASK Diagnostics, Inc., Norwell, MA (US)

( * ) Notice: Subject to any disclaimer, the term of this patent is extended or adjusted under 35 U.S.C. 154(b) by 0 days.

(21) Appl. No.: 13/672,099

(22) Filed: Nov. 8, 2012

(65) Prior Publication Data

US 2013/0065247 A1    Mar. 14, 2013

Related U.S. Application Data

(62) Division of application No. 12/811,435, filed as application No. PCT/US2008/014082 on Dec. 29, 2008, now Pat. No. 8,313,917.

(60) Provisional application No. 61/018,704, filed on Jan. 3, 2008.

(51) Int. Cl.
*G01N 33/00* (2006.01)

(52) U.S. Cl.
USPC .......... 435/7.94; 435/7.9; 435/7.92; 435/7.93

(58) Field of Classification Search
USPC ........................................ 435/7.9, 7.92–7.94
See application file for complete search history.

(56) References Cited

U.S. PATENT DOCUMENTS

| | | | |
|---|---|---|---|
| 5,786,451 A | 7/1998 | Thirkill | |
| 6,187,549 B1 | 2/2001 | Schmidt et al. | |
| 7,736,859 B2 * | 6/2010 | Reiter et al. | 435/7.1 |
| 2004/0191818 A1 | 9/2004 | O'Toole et al. | |
| 2006/0275794 A1 | 12/2006 | Carrino et al. | |
| 2007/0053893 A1 | 3/2007 | Schmidt | |
| 2008/0026394 A1 | 1/2008 | Labgold et al. | |

OTHER PUBLICATIONS

Ohkoshi et al., Uveitopathogenic sites in recoverin, 2001, Curr. Eye Res., vol. 22, Abstract.*
Palczewski et al., Ca2+-binding structure proteins in the retina: structure function and the etiology of human visual diseases, BioEssays 2000, 22:337-350, Abstract.
Polans et al., Recoverin, a photoreceptor-specific calcium binding protein, is expressed by the tumor of a patient with cancer-associated retinopathy, Proc. Natal. Acad. Sci. USA 1995, 92:9176-9180, Abstract.
Search Report of PCT/US2008/014082 filed Dec. 29, 2008.

* cited by examiner

*Primary Examiner* — Melanie Y Brown
*Assistant Examiner* — Erik B Crawford
(74) *Attorney, Agent, or Firm* — Novak Druce Connolly Bove + Quigg LLP

(57) ABSTRACT

Disclosed are procedures and methods for diagnosing latent and active cancers in a subject. The described methods include the use of sandwich ELISA assays containing antibodies specific for certain epitopes on the A-protein. This enables the assay to discriminate between the monomelic and homopolymeric forms of A-protein.

7 Claims, 1 Drawing Sheet

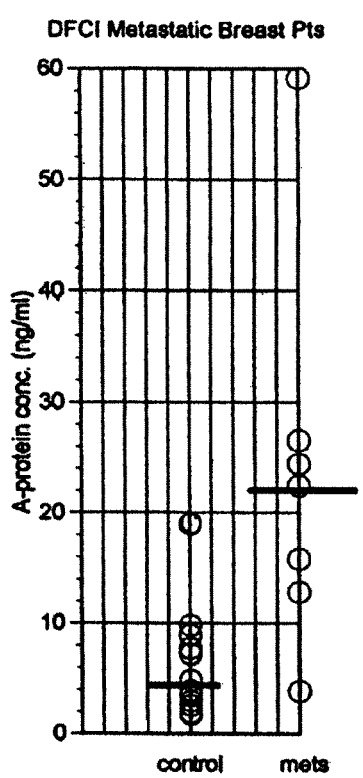

METHODS OF DIAGNOSING LATENT AND ACTIVE MALIGNANCIES

CROSS-REFERENCE TO RELATED APPLICATIONS

This application is a divisional application of U.S. patent application Ser. No. 12/811,435, filed Jul. 1, 2010, assigned U.S. Pat. No. 8,313,917, issue date Nov. 20, 2012.

BACKGROUND OF THE INVENTION

This invention relates to methods for diagnosing both latent and active cancers. More specifically, this invention relates to methods for diagnosing cancers by detecting the presence and relative amounts of isoforms of A-protein in a subject.

A-protein is a cellular enzyme that was first isolated from vertebrate rod photoreceptor cells by Schmidt et al., *Invest. Ophthalmol. Vis. Sci.*, 24:244 (1983). A-protein is also known in the scientific literature by the names $G_p$, Cockcroft, *Trends Biochem. Sci.*, 12:75-78 (1987); recoverin Dizhoor et al., *J. Biol. Chem.*, 267:16033-16036 (1992); and CAR protein, Thirkill et al., *Arch. Ophthalmol.*, 111:974-978 (1993). A-protein has been characterized as a GTP-binding protein (g-protein), Schmidt et al., *Invest. Ophthalmol. Vis. Sci.*, 28:94 (1987), that regulates phosphinositide metabolism by activating phospholipase C, Schmidt et al., *Invest Ophthalmol. Vis. Sci.*, 29:123 (1988).

A-protein exists in two forms; Schmidt et al., *Invest. Ophthalmol. Vis. Sci.*, 30:172 (1989); and Dizhoor et al., *J. Biol. Chem.*, 267:16033-16036 (1992): as a monomer of 26,000 daltons which is soluble in the cytosol, and as a co-synthetically modified form to which a fatty acid is attached by the action of the enzyme N-myristoyl transferase (NMT; E.C.2.3.1.97). The modified form of A-protein tends to self-associate as stable pentameric homopolymers with an approximate molecular weight of 130,000 daltons. These homoploymers are peripherally bound to the inner aspect of the cell membrane.

In its peripherally membrane-bound form, A-protein inactivated by a growth-factor receptor imbedded in the plasmalemma subsequent to activation of the receptor by a growth factor. The activation of this metabolic cascade mechanism results in a sustained release of calcium into the cytosol which ultimately stimulates the cell to divide. This general scheme is referred to as signal transduction (see U.S. Pat. No. 5,100,661).

In non-ocular tissues, A-protein transduces growth signals and is expressed in mitotically active cells including malignant tissues. A-protein is expressed inside affected malignant cells and in the blood stream. Fragments of the protein are also displayed on the surface of malignant cells. See Thirkill et al., *Invest. Ophthalmol. Vis. Sci.*, 33:2768-2772 (1992).

U.S. Patent Publication No. 20070053893, published Mar. 8, 2007, to Schmidt, discloses a method for reducing immunological tolerance to malignancy using formulations of myristoylCoA and N-myristoyl transferase to treat carcinomas displaying A-protein.

It will be readily appreciated that there exists a need for new and improved methods for diagnosing both potential or latent cancers and actual malignancies which may be difficult to detect using conventional diagnostic tools.

SUMMARY OF THE INVENTION

The present invention provides methods for detecting the presence of the pentomeric homopolymer of A-protein as a method for diagnosing latent pre-cancer disease in a mammal.

The present invention also provides methods for detecting the presence of the monomeric isoform of A-protein as a method for diagnosing an active malignancy in a mammal.

According to one aspect of the invention, the presence of the A-protein homopolymer is detected from a sample of biological fluid obtained from a mammal, preferably a human. The sample is introduced into a sandwich ELISA immunoassay which contains a capture antibody and a detectable antibody. The capture antibody and detectable antibody recognize the same epitope on the A-protein, said epitope having the sequence TDPKAYAQHV (SEQ ID NO:1). Excess unbound antibody is removed from the assay, and the amount of detectable antibody bound to the support surface is measured and compared to a standard for the assay. An abnormally high level of the pentomeric homopolymer detected is a direct measure of latent pre-cancerous disease in the mammal.

In a further aspect, the presence of the monomeric isoform of A-protein is detected from a sample of biological fluid obtained from a mammal, preferably a human. The sample is introduced into a sandwich ELISA immunoassay which contains a capture antibody and a detectable antibody. The capture antibody and detectable antibody recognize different epitopes on the A-protein. In this aspect, the capture antibody recognizes an epitope unique to the monomeric, unmodified isoforms of A-protein, while the detectable antibody recognizes the epitope having the sequence TDPKAYAQHV (SEQ ID NO:1). An abnormally high level of the monomeric form of A-protein detected compared to a standard is a direct measure of active malignancy in a subject.

Preferably, the antibodies used in the immunoassays are either monoclonal antibodies, or antibody fragments, such as Fab fragments. Humanized and engineered or recombinant antibodies can also be used in the immunoassay to advantage. The support surface can be a slide, plate or microtiter well. The individual immunoassay can also be part of a series of immunoassays conducted on multiple human subjects using robotic or automated techniques well known in the art for large volume assays.

Preferably, the detectable marker is a fluorescent dye or compound, or radioactive label, which can be readily detected and quantified using known techniques. The biological fluid can blood, serum, urine or lymph fluid.

In a still further aspect of the present invention, the antibodies described above are coupled to imaging agents using known techniques to allow clinicians to locate an active malignancy or the site of a latent malignancy.

BRIEF DESCRIPTION OF THE DRAWINGS

FIG. 1 is a plot of A-protein concentration for tissue samples obtained from normal patients or patients in remission (controls), and patients suffering from breast cancer.

DETAILED DESCRIPTION OF THE PREFERRED EMBODIMENTS

The present invention provides methods for the detection of both latent and active cancers in a mammal. The types of active cancers which can be treated by the formulations described herein include, but are not limited to, squamous cell carcinoma, small and large cell carcinoma of the lung, and breast, colon, cervical, and prostate carcinomas, as well as primary or metastatic tumors. As used herein, the term "primary tumor" refers to tumor growth at a first site and not secondary to growth elsewhere, while "metastatic tumor" refers to tumor growth at a site other than the original growth, caused by the migration of malignant cells from the first growth.

Unacylated or monomeric A-protein is expressed in the interior and on the surface of malignant cells, such as small and large cell carcinoma of the lung and breast, prostate, colon, cervical and squamous cell carcinomas. Acylation distinguishes the immunosuppressive (unacylated) form of A-protein from the immunogenic (acylated) form.

As used herein, the term "unacylated A-protein" refers to unmodified monomers of A-protein having an apparent molecular weight on polyacrylamide gels of 26,000 daltons.

The term "latent cancer" as used herein indicates that although the subject does not currently have an active form of cancer, the cancer is essentially dormant and a subject has a high propensity for developing cancer at some time during their life expectancy. The dormant cancer can be activated by any number of environmental or genetic triggers. The term "active cancer" indicates that the subject already has an active form of cancer which has not been previously detected using conventional testing protocols.

The present invention utilizes a sandwich ELISA (Enzyme-Linked ImmunoSorbent Assay) to detect the presence of the monomeric or homopolymeric forms of A-protein. The construction of such a sandwich immunoassay is well known to those skilled in the art.

Briefly, antibodies to the monomeric and/or homopolymeric form of A-protein can be obtained as described herein. One antibody is immobilized on a solid support (the "capture antibody"). The support is contacted with a sample of a biological fluid, and excess fluid is removed from the assay. An unknown amount of antigen (an isoform of A-protein) is immobilized on the solid support, and a second antibody (the "detection antibody") is contacted with the support, forming a complex with any antigen bound to the solid support. The detection antibody can be covalently linked to a suitable marker, such as an enzyme, a photochemical compound, or a radioactive compound. The marker is detected using a detectable signal such as a fluorescent chemical which emits fluorescent light when irradiated by a light source. The amount of fluorescence detected is a direct measure of the amount of antigen in the fluid sample.

The determination as to whether a particular cancer is latent, i.e. predisposed, or active depends on which particular isoform of A-protein is detected (monomeric or homopolymeric), and the amount of A-protein isoform so detected. The detection of the homopolymeric form in elevated levels as compared to a suitable reference standard is a positive indication that a subject has a latent form of cancer. Alternatively, the detection of the monomeric isoform of the antigen in elevated levels as compared to a reference standard is a positive indication that a subject has an active form of cancer.

The present invention can also be used to identify affected tissue in vivo. This can be achieved by coupling the antibodies described above to imaging agents using known techniques. The imaging agents of the invention are, in general, chemical entities which, when targeted to a tumor or process, can be detected using appropriate imaging instruments. The antibody/imaging agent complex is then used by a clinician to determine whether a mass is benign or malignant, and to locate metastatic cancer sites in vivo.

In one embodiment, antibodies to the monomeric, unacylated isoform of A-protein, and preferably antibodies to an epitope of A-protein that is unique and accessible only on the monomeric isoform of A-protein, are coupled to imaging agents and used as a diagnostic tool to locate active malignancies in a subject.

In another embodiment, antibodies to the homopolymeric, acylated isoform of A-protein, and preferably antibodies to the TDPKAYAQHV (SEQ ID NO:1) epitope of A-protein, are coupled to suitable imaging agents and used as a diagnostic tool to locate tissue within a subject having a latent predisposition for developing a malignancy.

By "subject" is generally meant, in the context of this application, a mammalian subject, and in particular, a human subject.

It is believed that antibodies against one isoform of A-protein are specific to that form and do not recognize the other isoform. It has now been discovered that the immunodominant epitope of A-protein that characterizes that homopolymeric form has the amino acid sequence TDPKAYAQHV (SEQ ID NO:1), and that the monomeric form has an epitope that is not accessible on the polymeric isoform. Consequently, a sandwich ELISA assay designed to detect the monomeric form of the protein has antibodies directed to different epitopes of the protein: a capture antibody specific for the unique monomeric epitope, and a detection antibody specific for the TDPKAYAQHV (SEQ ID NO:1) epitope. Alternatively, a sandwich ELISA assay designed to detect the homopolymeric isoform of the protein utilizes the same capture and detection antibodies, both being specific to the epitope having the sequence TDPKAYAQHV (SEQ ID NO:1), thus rendering the assay specific for the homopolymeric isoform.

In cancer cells, the regulatory pathway controlling cell division is generally absent, while this mechanism is present in normal mature cells. This results in the overproduction of A-protein and an upset of the normal equilibrium between the monomer and the polymer in cancer cells, increasing the relative amount of monomer in the cytoplasm of transformed cells relative to normal cells. It is believed that the lack of cellular differentiation seen in cancer cells causes the partial or total loss of the ability of the cell to modify A-protein, (see Olsen et al., *J. Biol. Chem.*, 260:3784-3790 (1985)), i.e. the change from immunoreactive, modified A-protein to immunosuppressant, unmodified A-protein correlates strongly with the earliest stages of tumor formation.

Antibodies to both the monomeric and homopolymeric isoforms of A-protein can be obtained using conventional techniques well known to those skilled in the art. Both monomeric and polymeric isoforms of A-protein can be obtained, for instance, from biological sources such as bovine retinas as described in more detail in Schmidt et al., *J. Biol. Chem.* 262:14333-14336 (1978).

Alternatively, isoforms of A-protein can be obtained by cloning a human genomic or retinal library according to the methods of Dizhoor et al., *J. Biol. Chem.*, 267:16033-16036 (1992). Briefly, this entails constructing oligonucleotide probes that are complementary to portions of the cDNA sequence of A-protein. See, for instance, Polans et al., *J. Biol. Chem.*, 112:981-989 (1991). The library is expanded by polymerase chain reaction and expressed in a host vector such as *E. coli* which has the human DNA subcloned into its chromosomes. Bacteria are grown in culture dishes and the plaques are screened with the positive plaques are selected and rescreened at least two more times. The gene product of selected plaques is checked for the correct sequence, corresponding to that of A-protein.

A-protein can also be cloned from a human genomic or retinal library according to the method of Ray et al., *Proc. Natl. Acad. Sci.*, 89:5705-5709 (1992). Briefly, this procedure entails constructing oligonucleotide probes that are complementary to portions of the cDNA sequence of A-protein. The library is expanded by polymerase chain reaction and expressed in a host vector such as *E. coli* which has the human DNA subcloned into it's chromosomes. Bacteria are grown in culture dishes and the plaques are screened with the oligonucleotide probes. Positive plaques are selected and rescreened two more times. The gene product of selected plaques is checked for the correct sequence, corresponding to that of A-protein.

EXAMPLE

A study is conducted using normal tissue specimens mixed with breast cancer tissue specimens. The normal tissue is obtained from normal patients and patients in cancer remission (no evidence of disease), and is used as a control in this experiment. All tissue samples are tested in triplicate, and the results are returned to the clinical investigator prior to breaking the code.

In the study of active malignancies, A-protein concentrations of more than 10 ng/ml are considered positive for the assay. The results of the study are shown in FIG. 1, in which numerical values are recorded and graphed. In FIG. 1, "Ned" indicates that there is no evidence of disease, while "Mets" indicates that the sample is diagnosed as having metastatic cancer.

As can be seen from FIG. 1, one specimen from the normal population is diagnosed as a positive; indicating that the donor has an undiagnosed cancer. One specimen from the identified breast cancer patients sampled, one patient tested negative for the active disease, but positive for the latent disease, demonstrating the higher level of information available to the clinician, and the ability of the present diagnostic techniques to discriminate between the metastatic recurrence of cancer from the non-recurrent forms.

Those skilled in the art will recognize, or be able to ascertain, using no more than routine experimentation, numerous equivalents to the specific substances and procedures described herein. Such equivalents are considered to be within the scope of this invention, and are covered by the appended claims. The patent and scientific literature referred to herein establishes the knowledge that is available to those with skill in the art. The issued U.S. patents, allowed applications, published foreign applications, and references cited herein are hereby incorporated by reference in their entirety.

What is claimed is:

1. A method for detecting the presence of the monomeric form of A-protein in a biological sample from a mammal, said sample containing both the polymeric and monomeric forms of A-protein, said method comprising the steps of:
    contacting the sample with an A-protein capture antibody bound to a support surface, said capture antibody recognizing an epitope of A-protein present on the monomeric form but not on the polymeric form of A-protein,
    removing excess sample from the support surface,
    contacting the support surface with an A-protein detectable antibody containing a detectable marker, said detectable antibody recognizing an epitope sequence consisting of SEQ ID NO:1,
    removing unbound antibody from the support surface, and
    determining the amount of detectable antibody bound to the support surface as a measure of the amount of the monomeric form of A-protein in the sample.

2. The method of claim 1 wherein all of the antibodies are monoclonal antibodies or antibody fragments.

3. The method of claim 1 wherein the support surface is a slide, plate or microtiter well.

4. The method of claim 1 wherein the detectable marker is a colorimetric enzyme, a fluorescent label or a radioactive label.

5. The method of claim 1 and wherein the sample is obtained from a bodily fluid.

6. The method of claim 1 wherein the mammal is a human subject.

7. The method of claim 5 wherein the fluid is selected from the group consisting of blood, serum, urine or lymph fluid.

* * * * *

UNITED STATES PATENT AND TRADEMARK OFFICE
CERTIFICATE OF CORRECTION

PATENT NO. : 8,445,220 B2
APPLICATION NO. : 13/672099
DATED : May 21, 2013
INVENTOR(S) : Geoffrey Schmidt It is certified that error appears in the above-identified patent and that said Letters Patent is hereby corrected as shown below:

In the Specifications:

Column 1, line 39, delete "inactivated" and insert therefor -- is activated --; and Column 2, line 42, after "can", insert -- be --.

Signed and Sealed this
Third Day of September, 2013

Teresa Stanek Rea
*Acting Director of the United States Patent and Trademark Office*

```
                      SEQUENCE LISTING

<160> NUMBER OF SEQ ID NOS: 1

<210> SEQ ID NO 1
<211> LENGTH: 10
<212> TYPE: PRT
<213> ORGANISM: Human
<220> FEATURE:
<221> NAME/KEY: protein
<222> LOCATION: (1)..(10)

<400> SEQUENCE: 1

Thr Asp Pro Lys Ala Tyr Ala Gln His Val
1               5                   10
```